US012681013B2

(12) United States Patent (10) Patent No.: US 12,681,013 B2
Yin et al. (45) Date of Patent: Jul. 14, 2026

(54) MICROFLUIDIC FLOW CHANNEL STRUCTURE, DETECTION SYSTEM AND METHOD FOR USING SAME

(71) Applicant: BOE TECHNOLOGY GROUP CO., LTD., Beijing (CN)

(72) Inventors: Yudan Yin, Beijing (CN); Jing Yu, Beijing (CN); Haonan Liu, Beijing (CN); Zhukai Liu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 738 days.

(21) Appl. No.: 17/928,663

(22) PCT Filed: May 12, 2021

(86) PCT No.: PCT/CN2021/093333
§ 371 (c)(1),
(2) Date: Nov. 30, 2022

(87) PCT Pub. No.: WO2021/249095
PCT Pub. Date: Dec. 16, 2021

(65) Prior Publication Data
US 2023/0176045 A1 Jun. 8, 2023

(30) Foreign Application Priority Data

Jun. 11, 2020 (CN) .......................... 202010529364.4

(51) Int. Cl.
*B01L 3/00* (2006.01)
*G01N 21/64* (2006.01)
*G01N 33/543* (2006.01)
(52) U.S. Cl.
CPC .. *G01N 33/54386* (2013.01); *B01L 3/502761* (2013.01); *G01N 21/6428* (2013.01);
(Continued)

(58) Field of Classification Search
CPC ......... G01N 33/54386; G01N 21/6428; G01N 21/6458; G01N 2021/6439; G01N 33/582;
(Continued)

(56) References Cited

U.S. PATENT DOCUMENTS

2002/0114738 A1 8/2002 Wyzgol
2007/0280856 A1 12/2007 Ulmanella et al.
(Continued)

FOREIGN PATENT DOCUMENTS

CN 104073428 A 10/2014
CN 105107401 A 12/2015
(Continued)

OTHER PUBLICATIONS

China Patent Office, First Office Action issued May 19, 2022 for application No. CN202010529364.4.
(Continued)

*Primary Examiner* — Christine T Mui
(74) *Attorney, Agent, or Firm* — HOUTTEMAN LAW LLC

(57) ABSTRACT

The present disclosure provides microfluidic flow channel structure, detection system and method for using detection system, aiming at improving uniformity of liquid introduction of microfluidic detection system. Microfluidic flow channel structure includes liquid inlet section (1), main chamber (3) and liquid outlet section (2), main chamber (3) includes liquid inlet end (31), chamber middle part (33) and liquid outlet end (32); liquid inlet section (1), liquid inlet end (31), chamber middle part (33), liquid outlet end (32) and liquid outlet section (2) are sequentially connected together; width of liquid inlet end (31) is gradually increased in direction from liquid inlet section (1) to chamber middle part (33); thinning flow guidance region (310) is provided at
(Continued)

edge of liquid inlet end (31) formed as width of liquid inlet end varies, and has thickness less than that of remaining region except thinning flow guidance region (310) of main chamber (3).

16 Claims, 4 Drawing Sheets

(52) U.S. Cl.
CPC .. *G01N 21/6458* (2013.01); *B01L 2200/0647* (2013.01); *B01L 2200/16* (2013.01); *B01L 2300/0654* (2013.01); *B01L 2400/084* (2013.01); *G01N 2021/6439* (2013.01)

(58) Field of Classification Search
CPC ... G01N 2021/0346; G01N 2021/6482; G01N 33/533; G01N 33/54306; B01L 3/502761; B01L 2200/0647; B01L 2200/16; B01L 2300/0654; B01L 2400/084; B01L 2300/0816; B01L 2300/0819; B01L 2300/0877; B01L 3/502715; B01L 3/5027; Y02A 50/30
USPC .................................................. 422/82.07, 50
See application file for complete search history.

(56) References Cited

U.S. PATENT DOCUMENTS

| | | |
|---|---|---|
| 2008/0257754 A1 | 10/2008 | Pugia |
| 2009/0016932 A1 | 1/2009 | Curcio et al. |
| 2014/0248618 A1 | 9/2014 | Shaikh et al. |
| 2015/0024373 A1 | 1/2015 | Xia et al. |
| 2015/0247845 A1 | 9/2015 | Heller et al. |
| 2016/0281126 A1 | 9/2016 | Qin et al. |
| 2018/0093268 A1 | 4/2018 | Meier et al. |

FOREIGN PATENT DOCUMENTS

| | | |
|---|---|---|
| CN | 106520537 A | 3/2017 |
| CN | 106955750 A | 7/2017 |
| CN | 107061240 A | 8/2017 |
| CN | 108686721 A | 10/2018 |
| CN | 108686724 A | 10/2018 |
| CN | 108816300 A | 11/2018 |
| CN | 208642696 U | 3/2019 |
| CN | 110058007 A | 7/2019 |
| CN | 110124758 A | 8/2019 |
| CN | 110257249 A | 9/2019 |
| CN | 110320355 A | 10/2019 |
| CN | 209727963 U | 12/2019 |
| CN | 110988331 A | 4/2020 |
| WO | 2014150853 A1 | 9/2014 |
| WO | 2016086374 A1 | 6/2016 |

OTHER PUBLICATIONS

China Patent Office, Second Office Action issued Dec. 2, 2022 for application No. CN202010529364.4.
Griffini et al., "Effect of microchannel plate design on fluid flow uniformity at low flow rates," Chem. Eng. Technol., Feb. 28, 2007, vol. 30, No. 3, pp. 395-406.
Zhao, Zhaoxi, "Flow channel design of droplet passive fusion in microfluidic chips," Mechanical Engineering, Sep. 10, 2014, pp. 9-11. English Abstract.
Wang et al., "Microfluidic network for research and application in life sciences," Progress in Chemistry, May 24, 2005, vol. 17, No. 3, Nankai Univ., Tianjun, China. English Abstract.
Gao et al., "Rapid detection of Haemophilus influenza based on microfluidic chip," Chin. J. Clin. Pathol., Mar. 30, 2020, vol. 12, No. 1, pp. 51-54. English Abstract.

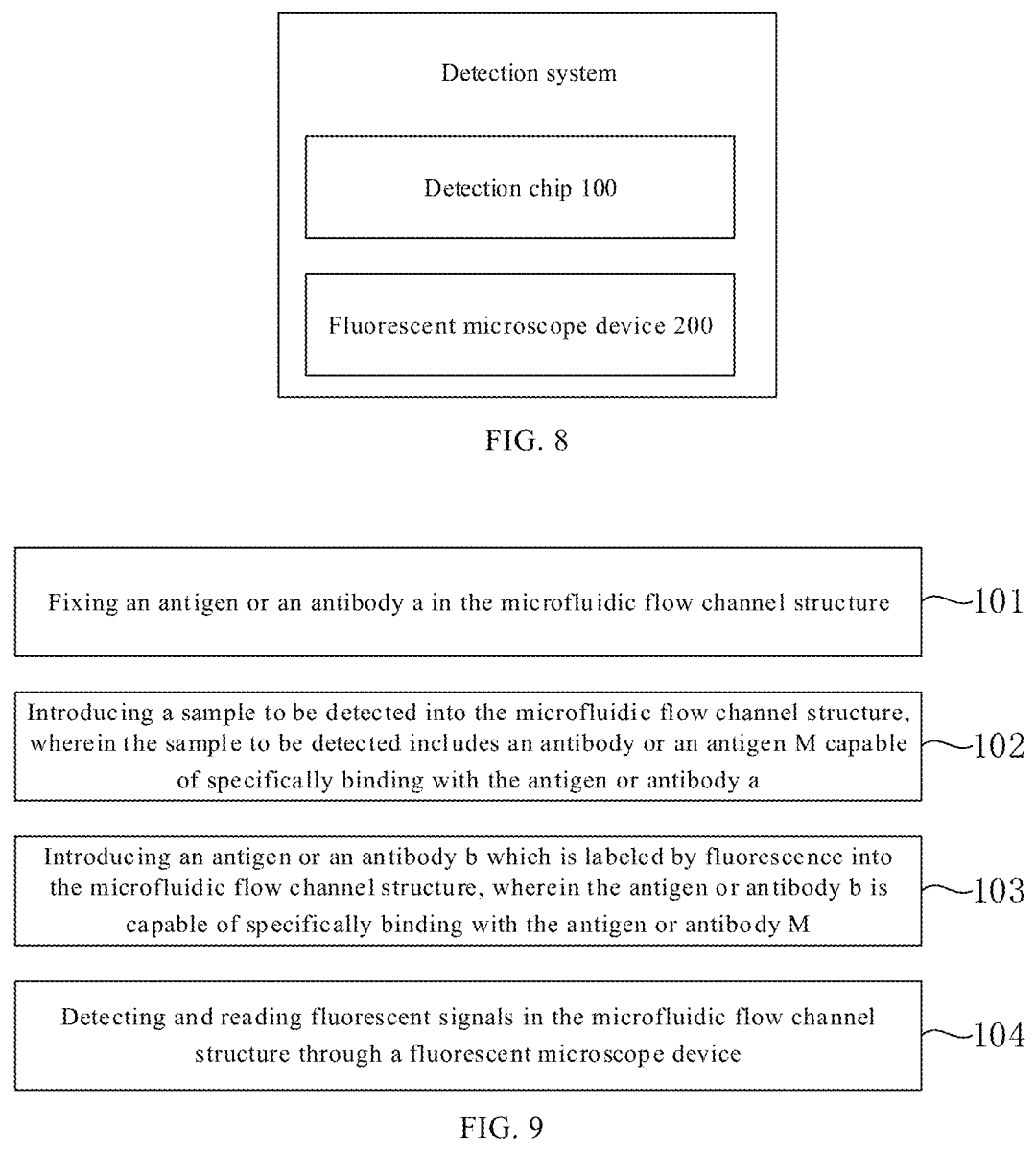

Detection system

Detection chip 100

Fluorescent microscope device 200

FIG. 8

Fixing an antigen or an antibody a in the microfluidic flow channel structure — 101

Introducing a sample to be detected into the microfluidic flow channel structure, wherein the sample to be detected includes an antibody or an antigen M capable of specifically binding with the antigen or antibody a — 102

Introducing an antigen or an antibody b which is labeled by fluorescence into the microfluidic flow channel structure, wherein the antigen or antibody b is capable of specifically binding with the antigen or antibody M — 103

Detecting and reading fluorescent signals in the microfluidic flow channel structure through a fluorescent microscope device — 104

FIG. 9

MICROFLUIDIC FLOW CHANNEL STRUCTURE, DETECTION SYSTEM AND METHOD FOR USING SAME

CROSS-REFERENCE TO RELATED APPLICATIONS

This is a National Phase Application filed under 35 U.S.C. 371 as a national stage of PCT/CN2021/093333, filed on May 12, 2021, an application claiming the priority of the Chinese Patent Application No. 202010529364.4 filed on Jun. 11, 2020 filed in the National Intellectual Property Administration, PRC, entitled "Microfluidic flow channel structure, detection system and method for using same", the content of which is incorporated herein by reference in its entirety.

TECHNICAL FIELD

The present disclosure relates to the field of microfluidic technology, in particular to a microfluidic flow channel structure, a detection system and a method for using a detection system.

BACKGROUND

A term "microfluidic chip" was originally introduced by Manz and Widmer in the 1990s to propose a micro total analysis system (μTAS). Professor Manz successfully applied the MEMS technology to the field of analytical chemistry and realized a high-speed capillary electrophoresis on microchips soon, the achievement is published in journals such as "Science" or the like. Hence, the field was rapidly gaining attention from the academic world and became one of the advanced science fields in the world. Lab on a chip and microfluidic chip are different terms proposed in this field. As the application of this subject expands from the initial analytical chemistry to a plurality of research and application fields, and researchers are deeply understanding this subject, the microfluidic chip has become a general term for this field.

Because the microfluidic chip has micro-structural characteristics, the problems of uneven distribution for samples, bubbles or sample retention or the like easily occur in a liquid inlet process, resulting in that the sample utilization rate and the detection yield are adversely influenced.

SUMMARY

The present disclosure provides a microfluidic flow channel structure, a detection system and a method for using a detection system, aiming at improving the uniformity of liquid introduction of a microfluidic detection system.

A microfluidic flow channel structure includes: a liquid inlet section, a main chamber and a liquid outlet section, wherein the main chamber comprises a liquid inlet end, a chamber middle part and a liquid outlet end; the liquid inlet section, the liquid inlet end, the chamber middle part, the liquid outlet end and the liquid outlet section are sequentially connected together; a width of the liquid inlet end is gradually increased in a direction from the liquid inlet section to the chamber middle part; the main chamber further comprises a thinning flow guidance region at an edge of the liquid inlet end formed as the width of the liquid inlet end varies, and the thinning flow guidance region has a thickness less than that of a remaining region of the main chamber except the thinning flow guidance region.

Optionally, the edge of the liquid inlet end has a circular arc shape; and the thinning flow guidance region is connected to the liquid inlet section and extends along the circular arc-shaped edge.

Optionally, the liquid inlet end has a semicircular shape, and the thinning flow guidance region is in a semicircular region at the edge of the liquid inlet end.

Optionally, a width of the liquid outlet end is gradually reduced in a direction from the chamber middle part to the liquid outlet section.

Optionally, the liquid outlet end has an isosceles triangle shape.

Optionally, the chamber middle part has a square shape; one side of two opposite sides of the square shape coincides with a chord length of the circular arc-shaped edge of the liquid inlet end, and the other side of the two opposite sides of the square shape coincides with a bottom side of the isosceles triangle shape of the liquid outlet end.

Optionally, the chamber middle part has a square shape.

Optionally, the remaining region of the main chamber except the thinning flow guidance region has a constant thickness.

Optionally, a ratio of the thickness of the thinning flow guidance region to a thickness of the remaining region of the main chamber is 0.2 to 0.5.

Optionally, the thickness of the thinning flow guidance region is gradually increased in a direction from an outer arc edge to an inner arc edge of the thinning flow guidance region, until the thickness of the thinning flow guidance region is equal to that of the remaining region of the main chamber except the thinning flow guidance region.

Optionally, the thinning flow guidance region has a uniform and constant thickness.

Optionally, a thickness of the liquid inlet section is equal to the thickness of the thinning flow guidance region.

Optionally, a thickness of the liquid outlet section is equal to that of the remaining region of the main chamber except the thinning flow guidance region.

Optionally, a ratio of the width of the thinning flow guidance region to a width of the liquid inlet section is 0.5 to 2.

Optionally, a width of the liquid outlet section is equal to a width of the liquid inlet section.

A detection system includes: a detection chip and a fluorescent microscope device; wherein the detection chip includes the microfluidic flow channel structure according to any one of the above embodiments; and the fluorescent microscope device is configured to detect and read fluorescent signals in the microfluidic flow channel structure.

A method for using a detection system, includes: fixing an antigen or an antibody a in the microfluidic flow channel structure according to any one of the above embodiments; introducing a sample to be detected into the microfluidic flow channel structure, wherein the sample to be detected comprises an antibody or an antigen M capable of specifically binding with the antigen or antibody a; introducing an antigen or an antibody b which is labeled by fluorescence into the microfluidic flow channel structure, wherein the antigen or antibody b is capable of specifically binding with the antigen or antibody M; and detecting and reading fluorescent signals in the microfluidic flow channel structure through a fluorescent microscope device.

BRIEF DESCRIPTION OF DRAWINGS

FIG. 8 is a block diagram of a detection system according to an embodiment of the present disclosure; and FIG. 9 is a flowchart of a method for using a detection system according to an embodiment of the present disclosure.

DETAIL DESCRIPTION OF EMBODIMENTS

Figure 1:
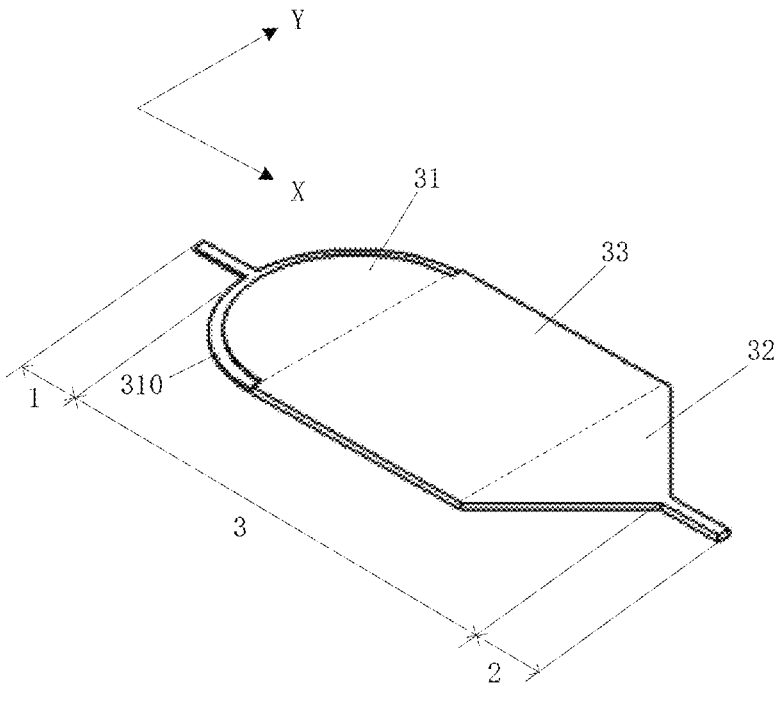
FIG. 1 is a schematic diagram of a microfluidic flow channel structure according to an embodiment of the present disclosure.

The technical solutions of the embodiments of the present disclosure will be described clearly and completely with reference to the drawings in the embodiments of the present disclosure. Obviously, the described embodiments are only some, not all, embodiments of the present disclosure. All other embodiments, obtained by one of ordinary skill in the art based on the embodiments in the present disclosure without any creative effort, belong to the protection scope of the present disclosure.

Specifically, the microfluidic flow channel structure provided by the present disclosure can provide an advanced sample introduction scheme for a microfluidic system required by in vitro diagnosis, drug property screening, cell culture, immunofluorescence detection or the like.

For example, the microfluidic flow channel structure may be used for immunoassay detection, or other detections having principle similar to immunological detection, such as detections based on antigen capture or aptamer capture. The immunoassay technology is a brand new concept generated by combining the specificity of the reaction of combination of antigen and antibody with a principle of a high-density integration of an electronic chip; belongs to a biological detection technology; and is an advanced detection method for obtaining biological information with a high flux in which a chip is prepared by arranging several, dozens, even tens of thousands or more antigens (or antibodies) in a high density, reaction is conducted among the antigens (or antibodies), a sample to be detected of a patient and a biological sample simultaneously, and detection results of all known antigens (or antibodies) in the chip are obtained at one time. Experimental principles include: a double antibody sandwich method immunochip, an indirect method immunochip, a competitive method immunechip, a PCR immunechip; according to the detection method, the experimental principles include: an enzyme-labeled immunechip, a radioisotope immunechip, a fluorescence immunechip, and a gold-labeled immunechip.

Specifically, the immunoassay and dPCR are two completely different technologies, although they are related to microfluidic chips. Specifically, the immunoassay relies on a specific capture for antigen and antibody, with emphasis on capture and detection; the dPCR relies on the amplification principle of nucleic acid, with emphasis on dispersion, uniformity and stability.

For example, in the immunoassay, the binding (such as binding efficiency and binding capacity) of antigen and antibody may be affected by the stability and uniformity of the fluid flow. The binding efficiency is low where a flow rate is great; the number of the samples in contact with the specific antibody or antigen is great, and the binding number per unit area is great where the flow rate is great. Therefore, if a detection result is comparable, for example, quantitatively comparable or comparable to a calibration chip, it is necessary to provide a parallelism and a stability for contacted samples in the unit area where each point or each detection point in a detection region is located. Therefore, the requirement for the uniformity of a sample introduction is high.

Figure 2:
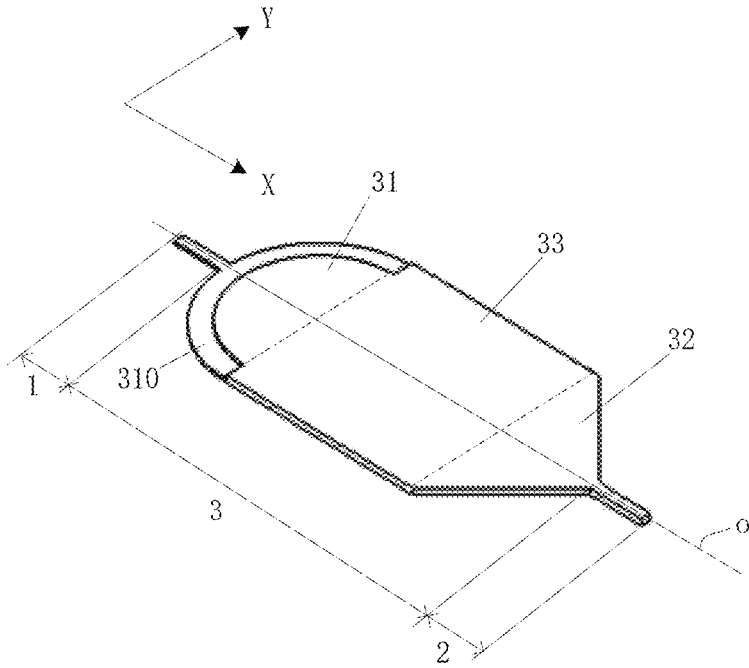
FIG. 2 is a schematic diagram of a microfluidic flow channel structure according to another embodiment of the present disclosure.

As shown in FIG. 1 and FIG. 2, an embodiment of the present disclosure provides a microfluidic flow channel structure, including: a liquid inlet section 1, a main chamber 3 and a liquid outlet section 2. The main chamber 3 includes a liquid inlet end 31, a chamber middle part 33 and a liquid outlet end 32; and the liquid inlet section 1, the liquid inlet end 31, the chamber middle part 33, the liquid outlet end 32 and the liquid outlet section 2 are sequentially connected together. In a direction from the liquid inlet section 1 to the chamber middle part 33, a width of the liquid inlet end 31 is gradually increased. A thinning flow guidance region 310 is provided at an edge of the liquid inlet end 31 formed as the width of the liquid inlet end varies, and has a thickness less than that of another region of the main chamber 3 except the thinning flow guidance region 310.

In the microfluidic flow channel structure provided in the embodiment of the present disclosure, the main chamber 3 may be configured as a reaction chamber for samples, the liquid inlet section 1 is configured as a liquid stabilizing section through which a sample liquid enters the main chamber 3, and the liquid outlet section 2 is configured as a residual liquid collecting section through which the reacted liquid flows out of the main chamber 3. Specifically, the sample liquid may enter the main chamber 3 through the liquid inlet section 1, react in the main chamber 3, and then, leave the main chamber 3 through the liquid outlet section 2.

In the microfluidic flow channel structure provided by the embodiment of the present disclosure, the main chamber 3 includes the liquid inlet end 31, the chamber middle part 33 and the liquid outlet end 32; the liquid inlet end 31 is connected to the liquid inlet section 1, the liquid outlet end 32 is connected to the liquid outlet section 2. The sample liquid firstly enters the liquid inlet end 31 through the liquid inlet section 1, then reaches the chamber middle part 33, finally reaches the liquid outlet section 2, and leaves the main chamber 3 through the liquid outlet section 2 connected to the liquid outlet end 32.

In the microfluidic flow channel structure provided by the embodiment of the present disclosure, in the direction from the liquid inlet section 1 to the chamber middle part 33, the width of the liquid inlet end 31 is gradually increased. The thinning flow guidance region 310 is provided at the edge of the liquid inlet end 31 formed as the width of the liquid inlet end varies. When the sample liquid enters the liquid inlet end 31, the sample liquid may diffuse along the thinning flow guidance region 310 at the edge of the liquid inlet end 31, and gradually diffuse to the inside of the main chamber 3. In this way, a uniform sample introduction for the liquid can be realized in the wider main chamber 3. Thus, the requirement of the immunoassay on the uniformity of the sample introduction can be satisfied well.

Compared with the existing modification technology, a design for the microfluidic flow channel structure provided by the embodiment of the present disclosure has the characteristics of stable sample introduction, difficulty in bubble generation, uniform liquid flow and the like. In addition, the flux for the immunoassay can be improved, a volume of the resident reagent and sample can be reduced, and the utilization of the reagent can be improved.

Figure 5:
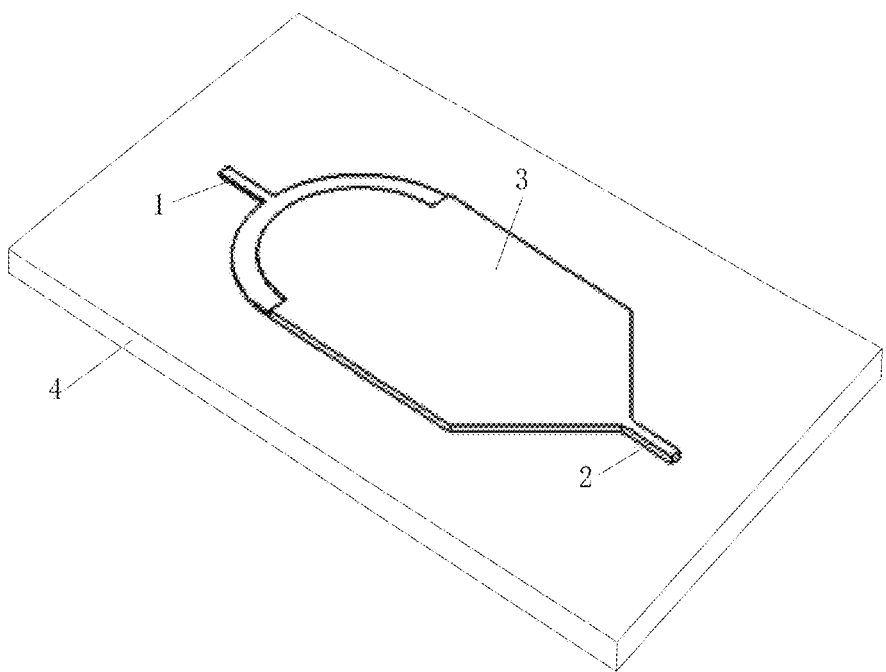
FIG. 5 is a schematic diagram of a detection chip according to an embodiment of the present disclosure.

Referring to FIG. 1 and FIG. 2, in the microfluidic flow channel structure provided in the embodiment of the present disclosure, the reaction main chamber 3 is a flat structure, and thus, can be applied to a flat chip, such as a flat chip 4 shown in FIG. 5. As shown in FIG. 1 and FIG. 2, in the microfluidic flow channel structure provided in the embodiment of the present disclosure, a "thickness" of each portion refers to a dimension of the portion along a direction perpendicular to the upper and lower flat surfaces (or the upper and lower surfaces of the flat chip). In the present disclosure, a "length direction" refers to a direction X along which the liquid runs/extends, and a "length" of each portion refers to a dimension of the portion along the direction X along which the liquid runs. Accordingly, a "width direction" refers to a direction Y perpendicular to the direction along which the liquid runs/extends, and a "width" of each portion refers to a dimension of the portion along the direction Y perpendicular to the direction along which the liquid runs/extends. Specifically, the portions include the liquid inlet section 1, the liquid inlet end 31, the chamber middle part 33, the liquid outlet end 32 and the liquid outlet section 2.

Specifically, both ends of the main chamber 3 along the length direction are connected to the liquid inlet section 1 and the liquid outlet section 2, respectively; a path along which the liquid entering the main chamber 3 flows is the liquid inlet end 31, the chamber middle part 33, and the liquid outlet end 32. In the path along which the liquid flows, the width of the liquid inlet end 31 is gradually increased until the liquid inlet end 31 is connected to the chamber middle part 33.

Referring to FIGS. 1 and 2, in one embodiment, the liquid inlet end 31 has two side edges, and the thinning flow guidance region 310 is connected to the liquid inlet section 1 and extends along the two side edges of the liquid inlet end 31. The sample liquid enters the thinning flow guidance region 310 from the liquid inlet section 1, and diffuses along the thinning flow guidance region 310 at the two side edges of the liquid inlet end 31, and gradually diffuses to the inside of the liquid inlet end 31, so that a uniform sample introduction from a narrower region to a wider region can be realized.

Referring to FIG. 1 and FIG. 2, in one embodiment, in the microfluidic flow channel structure of the present disclosure, the edge of the liquid inlet end 31 is designed to have a circular arc shape, that is, two side edges of the liquid inlet end 31 are in a circular arc shape in such a way that the width of the liquid inlet end 31 is gradually increased.

Further, the thinning flow guidance region 310 is connected to the liquid inlet section 1 and extends along the circular arc-shaped edges of the liquid inlet end 31.

In other words, the liquid inlet end 31 is located in a region inside the circular arc shape, and the thinning flow guidance region 310 is located adjacent to the liquid inlet end 31 and at the edge of the liquid inlet end 31, and thus, the thinning flow guidance region 310 is in the form of a circular arc region extending along the two side edges of the liquid inlet end 31. Thus, the generation of bubbles can be greatly reduced during the sample introduction of the liquid along the thinning flow guidance region 310 as the circular arc region.

Exemplarily, the liquid inlet end 31 is semicircular. The thinning flow guidance region 310 is a semicircular arc region.

Figure 3:
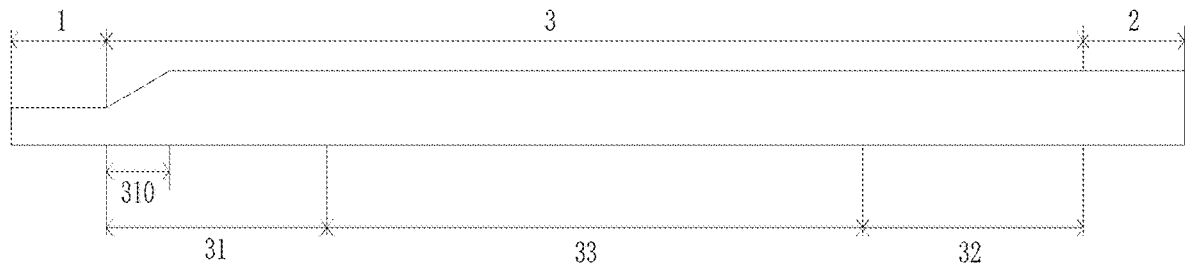
FIG. 3 is a schematic cross-sectional view of a microfluidic flow channel structure taken along a center line o according to an embodiment of the present disclosure.

Exemplarily, a thickness of the thinning flow guidance region 310 may gradually change; for example, as shown in FIG. 3, the thickness of the thinning flow guidance region 310 is gradually increased in a direction from an outer arc edge to an inner arc edge of the thinning flow guidance region 310, until the thickness of the thinning flow guidance region 310 is equal to that of another region of the main chamber 3 except the thinning flow guidance region 310. Specifically, the outer arc edge of the thinning flow guidance region 310 is the arc edge of the liquid inlet end 31, the inner edge of the thinning flow guidance region 310 is an edge connected to an inner region (another region of the main chamber 3) of the liquid inlet end 31, and a height of the inner edge of the thinning flow guidance region 310 is equal to that of the inner region of the liquid inlet end 31.

Figure 4:
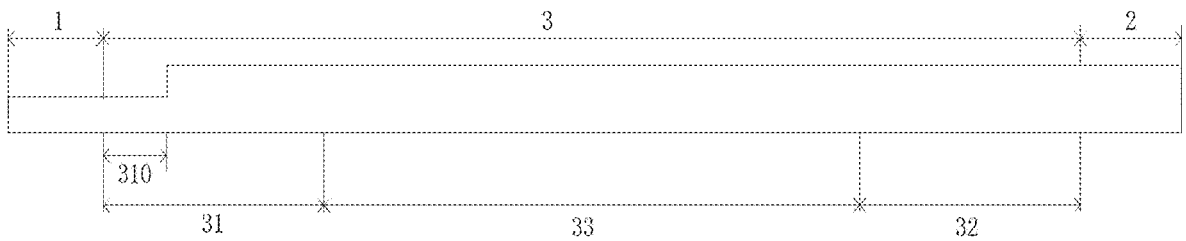
FIG. 4 is a schematic cross-sectional view of a microfluidic flow channel structure taken along a center line o according to another embodiment of the present disclosure.

Exemplarily, as shown in FIG. 4, the thickness of the thinning flow guidance region 310 may also be constant, i.e., a thickness of each portion in the thinning flow guidance region 310 is approximately constant.

Specifically, the edge of the liquid inlet end 31 is not limited to the circular arc shape, and may be linear. That is, the liquid inlet end 31 is not limited to the circular arc shape. For example, the liquid inlet end 31 may also be triangular or trapezoidal.

In one embodiment, a thickness of the liquid inlet section 1 is equal to the thickness of the thinning flow guidance region 310. Thus, the liquid sample can stably enter the thinning flow guidance region 310 from the liquid inlet section 1, and the generation of bubbles is reduced.

Specifically, as shown in FIG. 4, in a case where the thickness of each part in the thinning flow guidance region 310 is approximately constant, the thickness of the liquid inlet section 1 is equal to the thickness of the thinning flow guidance region 310, that is, the thickness of the liquid inlet section 1 is equal to the thickness of each part of the thinning flow guidance region 310. As shown in FIG. 3, when the thickness of the thinning flow guidance region 310 gradually varies, the expression that the thickness of the liquid inlet section 1 is equal to the thickness of the thinning flow guidance region 310 means that a thickness of the edge of the thinning flow guidance region 310 connected to the liquid inlet section 1 is equal to the thickness of the liquid inlet section 1.

Exemplarily, the thickness of the thinning flow guidance region 310 is 0.2 mm to 0.3 mm, for example, 0.2 mm, 0.24 mm, 0.28 mm, 0.3 mm; the thickness of the liquid inlet section 1 is 0.2 mm to 0.3 mm, and may be, for example, 0.2 mm, 0.24 mm, 0.28 mm, 0.3 mm. Specifically, for example, the thickness of each of the thinning flow guidance region 310 and the liquid inlet section 1 is 0.3 mm.

In one embodiment, a ratio of a width of the thinning flow guidance region 310 to a width of the liquid inlet section 1 is 0.5 to 2.

Specifically, the width of the thinning flow guidance region 310 refers to a dimension of the thinning flow guidance region 310 in a direction perpendicular to an extending direction thereof. For example, the thinning flow guidance region 310 extends in an arc shape and thus, is an arc-shaped region, and the width of the thinning flow guidance region 310 is the width of the arc-shaped region.

Exemplarily, the width of the thinning flow guidance region 310 is 1 mm to 2.5 mm, and may be 1 mm, 1.5 mm, 2.0 mm, 2.5 mm, for example. The width of the liquid inlet section 1 is 0.6 mm to 1.2 mm, and may be, for example, 0.6 mm, 0.8 mm, 1.0 mm, 1.2 mm.

Specifically, for example, as shown in FIG. 1, each of the width of the thinning flow guidance region 310 and the width of the liquid inlet section 1 may be 1 mm; alternatively, as shown in FIG. 2, the width of the thinning flow guidance region 310 is 2 mm, and the width of the liquid inlet section 1 is 1 mm.

In one embodiment, as shown in FIGS. 3 and 4, the another region of the main chamber 3 has a constant thickness, i.e. the region of the main chamber 3 other than the thinning flow guidance region 310 has a constant thickness. Thus, the liquid flow in the middle of the main chamber 3 can be kept approximately at the same liquid flow speed in a wider region, and the parallelism of the immunoassay can be guaranteed.

Exemplarily, the ratio of the thickness of the thinning flow guidance region 310 to a thickness of another region in the main chamber 3 is 0.2 to 0.5.

For example, the thickness of another region in the main chamber 3 is 0.5 mm to 0.8 mm, and may be, for example, 0.5 mm, 0.6 mm, 0.7 mm, 0.8 mm.

For example, the thickness of the thinning flow guidance region 310 is 0.3 mm; the thickness of the another region in the main chamber 3 is 0.6 mm.

In one embodiment, as shown in FIGS. 3 and 4, a thickness of the liquid outlet section 2 is equal to the thickness of the another region of the main chamber 3 (the region of the main chamber 3 other than the thinning flow guidance region 310).

Exemplarily, the thickness of the liquid outlet section 2 is 0.5 mm to 0.8 mm, and may be, for example, 0.5 mm, 0.6 mm, 0.7 mm, 0.8 mm. Specifically, for example, the thickness of the liquid outlet section 2 is 0.6 mm.

In one embodiment, as shown in FIG. 1 and FIG. 2, in the microfluidic flow channel structure of the present disclosure, a width of the liquid outlet end 32 gradually decreases in a direction from the chamber middle part 33 to the liquid outlet section 2. Therefore, the residual liquid can be conveniently collected so as to be conveniently discharged.

Exemplarily, the liquid outlet end 32 is triangular. For example, the liquid outlet end 32 has a shape of an isosceles triangle with a bottom edge connected to the chamber middle part 33.

Specifically, the liquid outlet end 32 of the main chamber 3 is not limited to be triangular, and may be a trapezoid or a shape having a circular arc edge.

In one embodiment, a width of the liquid outlet section 2 is equal to the width of the liquid inlet section 1.

Exemplarily, centerlines o of the liquid inlet section 1 and the liquid outlet section 2 are substantially aligned with each other, the centerline o is equal to the direction X along which the liquid runs. The main chamber 3 is symmetrical with respect to the centerline o, i.e. the liquid inlet end 31, the chamber middle part 33 and the liquid outlet end 32 are symmetrical with respect to the centerline o.

Exemplarily, the width of the liquid outlet section 2 is 0.6 mm to 1.2 mm, and may be, for example, 0.6 mm, 0.8 mm, 1.0 mm, 1.2 mm.

In one embodiment, as shown in FIGS. 1 and 2, the chamber middle part 33 is designed as a square shape, and a length of one side of the square close to the liquid inlet end 31 is equal to a chord length of the circular arc edge of the liquid inlet end 31.

For example, the chamber middle part 33 has a square shape.

Obviously, the chamber middle part 33 is not limited to a square shape, and may be in a trapezoidal shape, a polygonal shape, or an irregular shape having an arc-shaped edge.

Specifically, the liquid inlet end 31, the chamber middle part 33 and the liquid outlet end 32 are connected in sequence, and edges of the liquid inlet end 31, the chamber middle part 33 and the liquid outlet end 32 are smoothly connected to form the edge of the main chamber 3. In other words, the edge of the enclosed main chamber 3 is a smooth edge, without steps or sharp corners, etc., to avoid a retention of the liquid reagent.

For example, in the main chamber 3, the liquid inlet end 31 has a semicircular shape, the chamber middle part 33 has a square shape, and the liquid outlet end 32 has a isosceles triangle shape. Each of a radius of the semicircular liquid inlet end 31 and a length of the bottom side of the isosceles triangle of the liquid outlet end 32 is equal to a side length of the square chamber middle part 33, for example, each of the three may be about 20 mm. Two opposite sides of the square chamber middle part 33 coincide with the radius of the semicircular liquid inlet end 31 and the bottom side of the isosceles triangle of the liquid outlet end 32, respectively.

It should be noted that references to "constant" in this application, such as "constant length", constant width", "constant thickness", or the like, specifically means that values are substantially the same with a certain error, where the value error is within a range of variation. For example, if one length value is within 5% error around the other length value, both of the two length values may be referred to as equal to each other.

Specifically, an embodiment of the present disclosure further provides a detection chip, and as shown in FIG. 5, the detection chip 4 includes the microfluidic flow channel structure in any one of the embodiments described above.

Exemplarily, the detection chip may include a liquid inlet and a liquid outlet, the liquid inlet is connected to the liquid inlet section 1, and the liquid outlet is connected to the liquid outlet section 2. The solution for the reaction system may be injected into the liquid inlet through a micro-injection pump or a pipette, then enter the microfluidic flow channel structure, and flows out of the microfluidic flow channel structure through the liquid outlet after reacting in the main chamber 3.

Figure 6:
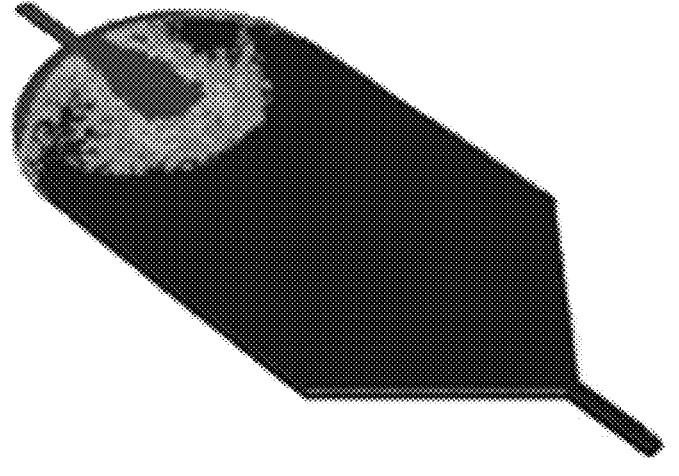
FIG. 6 is a schematic diagram of a simulation for a liquid introduction effect of a microfluidic flow channel structure according to an embodiment of the present disclosure.
Figure 7:
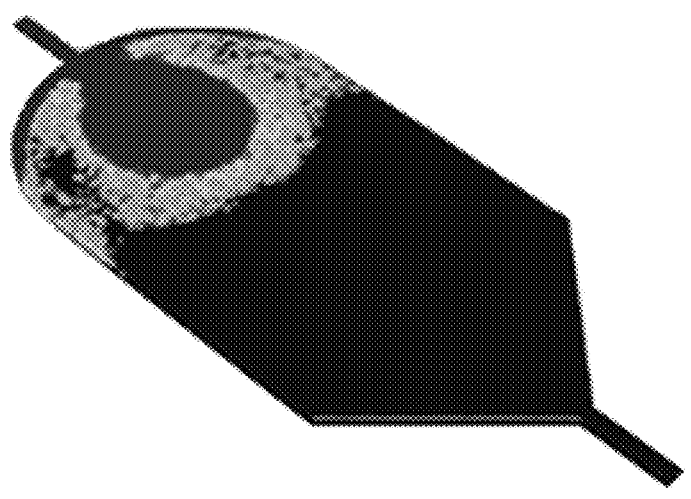
FIG. 7 is another schematic diagram of a simulation for a liquid introduction effect of a microfluidic flow channel structure according to an embodiment of the present disclosure.

In order to explain the effect of the sample introduction of the microfluidic flow channel structure provided by the present disclosure, the inventor of the present disclosure utilizes a professional fluid simulation software "Ansys Fluent" to perform a simulation evaluation on the actual effect of the microfluidic flow channel structure provided by the present disclosure. Specifically, FIGS. 6 and 7 are schematic diagrams of a simulation for an effect of a sample introduction of the microfluidic flow channel structure shown in FIG. 1. Specifically, the liquid inlet end has a semicircular shape, the chamber middle part has a square shape, and the liquid outlet end has an isosceles triangle shape, and the width of the thinning flow guidance region is 1 mm. FIG. 6 is an effect diagram of the sample introduction operation for 15 s, and FIG. 7 is an effect diagram of the sample introduction operation for 20 s. As can be seen from FIG. 6 and FIG. 7, when the sample liquid enters the liquid inlet end, due to the existence of the thinning flow guidance region, the sample liquid preferentially diffuses to both sides, and then flows parallelly to the inside of the main chamber as a whole, so that a relatively uniform sample introduction is realized, and the liquid flow is kept at the approximately same flow speed in a wider region, thereby satisfying the requirement of the immunoassay on the uniformity of the sample introduction well.

In addition, for the detection chip adopting the microfluidic flow channel structure of the embodiment of the present disclosure, the inventor also carries out an actual experiment for the sample introduction operation, during which it can be intuitively seen that the sample liquid preferentially diffuses to both sides, and then flows parallelly to the inside of the main chamber as a whole, the sample introduction is relatively uniformed, and the liquid flow in the chamber middle part is kept at the approximately same flow speed in a wider region, thereby satisfying the design requirement.

Specifically, the detection chip provided by the present disclosure is a flat chip; the detection chip may be used for immunoassay detections, or other detections having a similar principle to immunoassay, such as detections based on antigen capture or aptamer capture.

Specifically, an embodiment of the present disclosure further provides a detection system, as shown in FIG. 8, including a detection chip 100, which includes the microfluidic flow channel structure in any one of the above embodiments.

For example, the detection system provided by the embodiments of the present disclosure is an immunoassay system.

For example, the detection system provided in the embodiment of the present disclosure may further include a detection device. In particular, the result is generally detected by an optical method. As shown in FIG. 8, for example, a fluorescent microscope device 200 may be used in the present disclosure to detect and read fluorescent signals in the microfluidic flow channel structure for subsequent analysis.

For example, the detection system provided in the embodiment of the present disclosure may further include: 1, a matching reagent (kit) often required to be replaced or mix reagents in the immunoassay, which may refer to a method for using a detection system below; 2, a fluid driving device, except a few chip products using capillary phenomenon for automatic liquid suction, the chip is often required to drive a sample, a reagent, a buffer solution, a cleaning solution or the like which are possibly needed in the detection by using an external machine or/and a pipeline system including pumps and valves.

Specifically, the detection system may further include a waste liquid recovery device, a temperature control device, or the like, which may be specifically set as needed, and are not described herein.

Specifically, an embodiment of the present disclosure further provides a method for using a detection system, as shown in FIG. 9, the method includes the following steps: Step 101, fixing an antigen or an antibody a in the microfluidic flow channel structure according to any one of the above embodiments; Step 102, introducing a sample to be detected into the microfluidic flow channel structure, wherein the sample to be detected includes an antibody or an antigen M capable of specifically binding with the antigen or antibody a; Step 103, introducing an antigen or an antibody b which is labeled by fluorescence into the microfluidic flow channel structure, wherein the antigen or antibody b is capable of specifically binding with the antigen or antibody M; and Step 104, detecting and reading fluorescent signals in the microfluidic flow channel structure through a fluorescent microscope device.

Specifically, in the embodiment of the present disclosure, the method for the immunoassay is realized through the detection system. The immunoassay principle is the specific binding of antigen and antibody; when the principle is used for detection, the antibody may be preset to detect the antigen, and the antigen may be preset to detect the antibody, which is set as needed. Alternatively, the same principle may be realized by using different detection methods, such as, enzyme-linked immunosorbent assay (ELISA), and details are not repeated here.

For example, in the embodiment of the present disclosure, a double antibody sandwich method is used. In a simplified manner, assuming that an antigen M to be detected has two antigenic determinants A and B, and two corresponding antibodies a and b may specifically bind to the antigenic determinants A and B. Optionally, the antibody a may be chemically or physically fixed on a surface of a detection region of a chip (the inner surface of the main chamber of the microfluidic flow channel structure); then a sample containing antigens M to be detected flows through the detection region; some antigens M is captured by the antibody a and is fixed; then a fluorescent-labeled antibody b is introduced into the chip; the antibody b may also bind to the antigens M; the fixed antigens M may continue to capture the antibody b; and finally, washing is performed (the captured antigen and antibody cannot be washed away). In this way, if fluorescence is found by a fluorescence detection, the sample contains the antigens M. Specifically, the microfluidic flow channel structure in the application is designed so that the sample introduction of the main chamber is uniform, and thus, it can provide parallelism and a stability for contacted samples in the unit area where each point or each detection point in the detection region (the main chamber) is located. Further, it can improve the accuracy of the detection result.

Obviously, the detection system provided by the embodiment of the present disclosure is not limited to be applied to the above method, that is, the method for the detection system is not limited to be used for the immunoassay, and may also be applied to other detections having a similar principle to immunoassay, such as detections based on antigen capture or aptamer capture.

It should be noted that in some embodiments of the present disclosure, the detection chip and the detection system may further include other structures, which may be determined according to actual requirements and are not described herein. In addition, a structural shape, a size proportion, or the like of the microfluidic flow channel structure are not limited to those described in the above embodiments, and may be specifically adjusted according to actual needs, which is not limited in the embodiments of the present disclosure. In addition, the drawings in the present disclosure are only used for schematically illustrating the structural shape and approximate proportion thereof, and do not limit the specific size and proportion of the microfluidic flow channel structure according to the embodiments of the present disclosure.

It will be apparent to one of ordinary skill in the art that various changes and modifications may be made in the embodiments of the present disclosure without departing from the spirit and scope of the present disclosure. Thus, if such changes and modifications of the present disclosure fall within the scope of the claims of the present disclosure and their equivalents, the present disclosure is intended to include such changes and modifications.

What is claimed is:

1. A microfluidic flow channel structure, comprising:

a liquid inlet section, a main chamber and a liquid outlet section, wherein the main chamber comprises a liquid inlet end, a chamber middle part and a liquid outlet end;

the liquid inlet section, the liquid inlet end, the chamber middle part, the liquid outlet end and the liquid outlet section are sequentially connected together;

a width of the liquid inlet end is gradually increased in a direction from the liquid inlet section to the chamber middle part;

the main chamber further comprises a thinning flow guidance region at an edge of the liquid inlet end formed as the width of the liquid inlet end varies, and the thinning flow guidance region has a thickness less than that of a remaining region of the main chamber except the thinning flow guidance region, a width of the liquid inlet section and a width of the liquid outlet section are constant and less than a width of the main chamber, a bottom surface of the liquid inlet section, a bottom surface of the main chamber and a bottom surface of the liquid outlet section are coplanar, a level of a top surface of the liquid inlet section is lower than a level of a top surface of the main chamber and a level of a top surface of the liquid outlet section, and a top surface of a portion of the main chamber other than the thinning flow guidance region is coplanar with the top surface of the liquid outlet section.

2. The microfluidic flow channel structure according to claim 1, wherein the liquid inlet end has a circular arc-shaped edge; and the thinning flow guidance region is connected to the liquid inlet section and extends along the circular arc-shaped edge.

3. The microfluidic flow channel structure according to claim 2, wherein the liquid inlet end has a semicircular shape, and the thinning flow guidance region is in a semicircular region at the edge of the liquid inlet end.

4. The microfluidic flow channel structure according to claim 2, wherein a width of the liquid outlet end is gradually reduced in a direction from the chamber middle part to the liquid outlet section.

5. The microfluidic flow channel structure according to claim 4, wherein the liquid outlet end has an isosceles triangle shape.

6. The microfluidic flow channel structure according to claim 5, wherein the chamber middle part has a square shape;

one side of two opposite sides of the square shape coincides with a chord length of the circular arc-shaped edge of the liquid inlet end, and the other side of the two opposite sides of the square shape coincides with a bottom side of the isosceles triangle shape of the liquid outlet end.

7. The microfluidic flow channel structure according to claim 1, wherein a ratio of a thickness of the thinning flow guidance region to a thickness of the portion of the main chamber other than the thinning flow guidance region is 0.2 to 0.5.

8. The microfluidic flow channel structure according to claim 1, wherein a thickness of the thinning flow guidance region is gradually increased in a direction from an outer arc edge to an inner arc edge of the thinning flow guidance region, until the thickness of the thinning flow guidance region is equal to that of the portion of the main chamber other than the thinning flow guidance region.

9. The microfluidic flow channel structure according to claim 1, wherein the thinning flow guidance region has a uniform and constant thickness.

10. The microfluidic flow channel structure according to claim 2, wherein a thickness of the liquid inlet section is equal to the thickness of the thinning flow guidance region.

11. The microfluidic flow channel structure according to claim 2, wherein a ratio of the width of the thinning flow guidance region to a width of the liquid inlet section is 0.5 to 2.

12. The microfluidic flow channel structure according to claim 1, wherein a width of the liquid outlet section is equal to a width of the liquid inlet section.

13. A detection system, comprising:

a detection chip and a fluorescent microscope device;

wherein the detection chip comprises the microfluidic flow channel structure according to claim 1; and the fluorescent microscope device is configured to detect and read fluorescent signals in the microfluidic flow channel structure.

14. A method for using a detection system, comprising:

fixing a first antigen or a first antibody in the microfluidic flow channel structure according to claim 1;

introducing a sample to be detected into the microfluidic flow channel structure, wherein the sample to be detected comprises a second antibody or a second antigen capable of specifically binding with the first antigen or the first antibody;

introducing a third antigen or a third antibody which is labeled by fluorescence into the microfluidic flow channel structure, wherein the third antigen or the third antibody b is capable of specifically binding with the second antigen or the second antibody; and detecting and reading fluorescent signals in the microfluidic flow channel structure through a fluorescent microscope device.

15. The microfluidic flow channel structure according to claim 3, wherein a width of the liquid outlet end is gradually reduced in a direction from the chamber middle part to the liquid outlet section.

16. The microfluidic flow channel structure according to claim 3, wherein the remaining region of the main chamber except the thinning flow guidance region has a constant thickness.

* * * * *